United States Patent [19]

Olsen

[11] Patent Number: 4,687,176

[45] Date of Patent: Aug. 18, 1987

[54] FLOW CONTROL VALVE FOR A FLEXIBLE WALLED TUBE

[76] Inventor: C. E. Olsen, 5521 Canalino Dr., Carpenteria, Calif. 93013

[21] Appl. No.: 882,840

[22] Filed: Jul. 7, 1986

[51] Int. Cl.$^4$ ............................................. F16K 7/06
[52] U.S. Cl. ...................................... 251/9; 251/340
[58] Field of Search ................... 251/4, 6, 8, 251, 254, 251/256, 9, 340; 138/119

[56] References Cited

U.S. PATENT DOCUMENTS

| | | | |
|---|---|---|---|
| 2,518,625 | 8/1950 | Langstaff | 251/5 |
| 3,410,517 | 11/1968 | Wall | 251/6 |
| 3,612,474 | 10/1971 | Strohl, Jr. | 251/9 |
| 3,685,786 | 8/1972 | Woodson | 251/4 |
| 4,205,819 | 6/1980 | Soika | 251/9 |
| 4,453,653 | 6/1984 | Chapelsky et al. | 138/119 |
| 4,512,545 | 4/1985 | Mar | 251/4 |

FOREIGN PATENT DOCUMENTS 500322 11/1954 Italy ......................................... 251/8

Primary Examiner—Martin P. Schwadron
Attorney, Agent, or Firm—Jack C. Munro

[57] ABSTRACT

A flow control valve for a flexible walled tubing to control and regulate the rate of flow of a fluid through the tubing which comprises a pair of movable fingers which are pressed against a thermally deformed flaccid section of the tubing to vary the cross-sectional size of the bore within the tubing thereby controlling the volume of flow of the fluid through the tubing. This flow control valve is particularly useful in administering liquids for intravenous feeding and other medical purposes.

11 Claims, 4 Drawing Figures

FLOW CONTROL VALVE FOR A FLEXIBLE WALLED TUBE

BACKGROUND OF THE INVENTION

The field of this invention relates to a flow control valve to be usable in conjunction with a flexible walled tube to regulate the rate of flow of fluid through the tube.

In the administration of fluid into a human body for a medical purpose, it is customary to store a quantity of the fluid that is to be supplied to the human body within a container such as a bottle, plastic bag or other similar container. The typical way in which this is supplied to the human body is intravenously. The typical way that the fluid is administered intravenously is that the container is located at a height greater than the patient. The fluid within the container is then permitted to flow by gravity through a flexible walled tube and through a needle which has been entered within a vein of the human being. It is common for the patient's physician to require that the contained fluid be incrementally metered to the patient in terms of a given number of drops of fluid per minute. With adults, this number of drops per minute can be very small and with pediatric patients, the flow rate can be even smaller.

In the past, there has been utilized in conjunction with the tubing a pinch valve assembly which would pinch a portion of the tubing in order to meter the amount of fluid being given to the patient. Such pinch valves usually utilize a roller which presses against the tubing. It has been found that when this roller is set to administer to the patient a certain number of drops per minute of the liquid, that it doesn't take long, such as within fifteen or twenty minutes, that this number of drops per minute is increased. As a result, within a hospital, it is common practice for a nurse to continuously move from patient to patient constantly checking such valves to make sure that the flow rate is maintained at its precise established level. For example, if a patient is being administered with thirty drops per minute of fluid, it doesn't take much of a movement within the valve to result in the patient receiving forty to fifty drops per minute.

The reason in the past that conventional valves have been difficult to be set and remain set is that the valve itself is encountering continuous pressure by the fluid pressing against the valve. This continuous pressure, though small, over a period of time will cause the valve to actually move a minute amount. This is referred to as "creep". It does not take much of an amount of movement to result in a substantially increased percentage of flow into the patient.

Additionally, the flexible walled tubing, which is usually formed of plastic, has an inherent characteristic of wanting to return to its original shape rather than its "pinched" configuration. This tendency to return to its original shape is referred to as "cold flow" of the material. Because of this "cold flow" and "creep", conventionally used valves are just not capable of precisely regulating over a period of time the amount of fluid that is being administered to a patient.

The use of such a valve in conjunction with intravenous feeding equipment in the past has been rather an inexpensive part of the equipment. At the most, such a valve would cost only a few dollars. However, if a hospital wished to insure that a patient was receiving a precisely controlled amount of fluid, it was necessary for the hospital to purchase a flow regulating monitoring apparatus which was quite complicated. There is no doubt that such a monitoring apparatus would precisely control the flow of fluid to a patient and such devices are frequently used in a life-threatening situation. However, such devices are quite expensive. It would be most desirable if an inexpensive type of valve could be manufactured which would be able to achieve the high degree of precision of the expensive flow monitoring apparatuses which are now in current widespread use within hospitals.

SUMMARY OF THE INVENTION

The present invention relates to an improved flow control valve for external use on a flexible walled tube for regulating the flow of a fluid through the tube. The valve of the present invention is designed to be utilized in conjunction with a portion of the tube which is thermally deformed to assume a non-circular configuration and a flaccid shape. In other words, the tube has lost its "memory". About this flaccid section of tubing there is mounted an inner tubular member. A portion of this inner tubular member includes a pair of deflectable fingers. One of the fingers includes a concave section with the other of the fingers including a convex section. Pressing of the fingers together presses the tube an even amount across its entire cross-section. A collet is mounted about the inner tubular member and is screw threadingly secured thereto. The collet is capable of being moved by the screw threaded arrangement relative to the inner tubular member. The collet includes a cam surface in the form of a conical tapered surface. This conical tapered surface is to contact the deflectable fingers. Screw threading movement of the collet with respect to the inner tubular member results in the tapered surface pressing against the fingers thereby deflecting such and decreasing the cross-sectional size of the tube thereby regulating the amount of fluid that is being permitted to flow through the tube.

The primary objective of the present invention is to construct a flow control valve which is capable of regulating a precise quantity of fluid to be administered to a patient intravenously and, once established at a particular regulating value, that particular volume of fluid flow will be continuously administered over an extended period of time.

Another objective of the present invention is to provide a flow control valve which can be easily manipulated with one hand of the user.

It is another object of the present invention to provide a flow control valve which is of simple construction and therefore can be manufactured inexpensively.

DETAILED DESCRIPTION OF THE SHOWN EMBODIMENT

Figure 1:
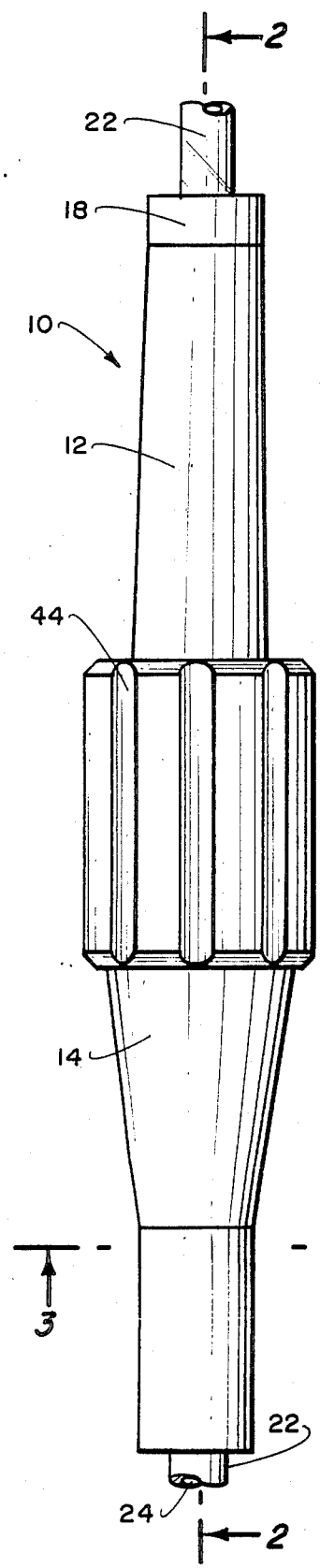
FIG. 1 is a side elevational view of the flow control valve of the present invention showing how the valve would appear in its exterior configuration.

Referring particularly to the drawing, there is shown the flow control valve 10 of this invention which is formed primarily of an inner tubular member 12 and a collet 14. Both the inner tubular member 12 and the collet 14 will be constructed of a rigid moldable material such as plastic.

The inner tubular member 12 has an axial bore 16 which is open at both its inner end and its outer end. The outer end is closed by a plug 18. The plug 18 includes a central opening 20 within which is fixedly mounted a tube 22. The tube 22 is constructed of a plastic material and has a bore 24 through which is to be conducted a fluid from a source (not shown) to be deposited at a depositing location (not shown).

The type of plastic for the tube 22 can be varied with possibly one particular type of plastic being preferred. However, an important consideration is that if a section of the tube 22 is subjected to a certain elevated temperature, that section of the tube 22 will assume a flaccid configuration. Such a flaccid section as is shown at 26 within the drawing. Basically, the section 22 has lost its memory and in its normal at-rest position the bore 24 within the section 26 is non-circular which is different from the remaining section of the tube 22.

This flaccid section 26 is located at the inner end of the inner tubular member 12. The inner end of the tubular member 12 is formed into a pair of fingers 28 and 30. The fingers 28 and 30 oppose each other and are capable of being readily deflected toward each other. The interior surface 32 of the finger 28 is formed concave. The interior surface 34 of the finger 30 is formed convex. If the convex surface 34 would be permitted to rest within the concave surface 32, such would closely conform thereto. However, in actual practice, this does not occur as the flaccid section 26 will be located between the surfaces 32 and 34.

Formed on the exterior surface of the inner tubular member 12 is a threaded section 36. The collet 14 includes an axial bore 38. This axial bore 38 is open-ended. A portion of this axial bore 38 includes a threaded section 40. The threaded section 40 is in continuous engagement with the threaded section 36. Rotative movement of the collet 14 relative to the inner tubular member 12 will result in longitudinal movement between the collet 14 and the inner tubular member 12.

A portion of the axial bore 38 includes a cam surface 42. This cam surface 42 defines a section of a cone so that the surface 42 assumes a conically tapered configuration. This cam surface 42 is to be in continuous contact with the exterior surface of the fingers 28 and 30.

Figure 2:
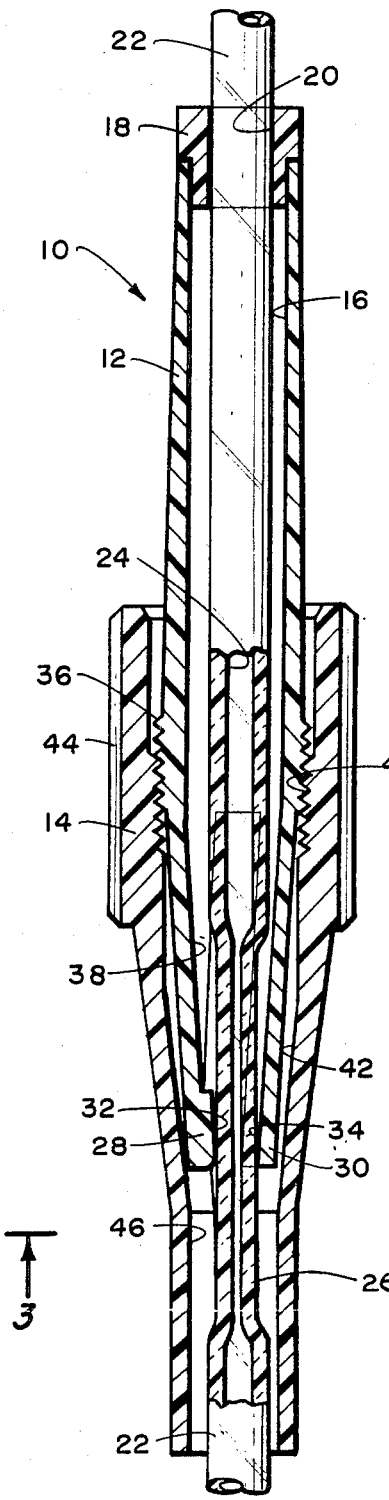
FIG. 2 is a longitudinal cross-sectional view through the flow control valve of the present invention taken along line 2—2 of FIG. 1 showing the valve in a position permitting a limited flow of fluid to be conducted through the tubing upon which the valve is mounted.
Figure 3:
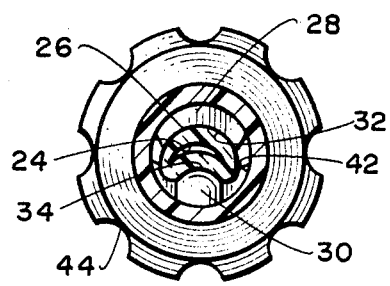
FIG. 3 is a transverse cross-sectional view taken along line 3—3 of FIG. 1.
Figure 4:
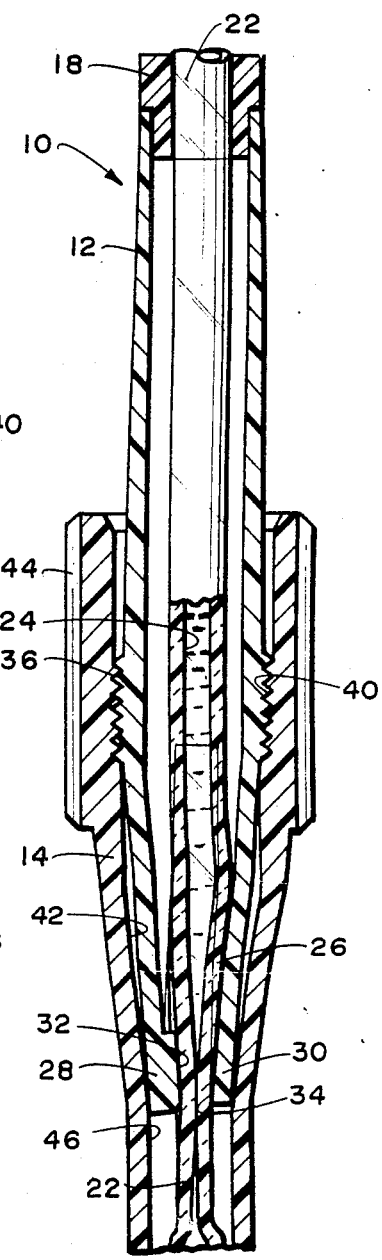
FIG. 4 is a cross-sectional view similar to that of FIG. 2, but showing the valve in a completely closed position.

The operation of the flow control valve of this invention is as follows: Let it be assumed that the valve 10 of this invention is located at the position shown in FIG. 2 of the drawing. In this particular position, the flow of fluid is being conducted through the bore 24 of the tube 22 and is metered through the flaccid section 26 to be deposited at a desired location such as within an intravenous feeding needle which has been mounted within the body of a human being. Let it now be assumed that it is desired to decrease the amount of flow that is being conducted to the human being. The operator only needs to rotate the collet 14 relative to the inner tubular member 12. This rotation is achieved manually and grooves 44 are provided within the exterior surface of the collet 14 in order to facilitate this manual movement. When the collet 14 is turned, the user holds in a fixed position the inner tubular member 12. The rotation of the collet 14 should be in the direction to cause the fingers 28 and 30 to move toward the open end 46 of the collet 14. Movement in this direction causes fingers 28 and 30 to be moved toward each other since they are riding on the cam surface 42 and this cam surface 42 gets narrower as it approaches opening 46. When the fingers 28 and 30 move toward each other, there is pressed therebetween the flaccid section 26 of the tube 22. As a result, the bore 24 located within the flaccid section 26 is decreased in cross-sectional size. Hence, the volume of fluid which can flow through this section of the bore 24 is decreased depending upon the amount of threading movement between the collet 14 and the inner tubular bore 12 the volume of the fluid passing through the flaccid section 26 can be precisely controlled. In other words, the operator can precisely determine how many drops per minute is being conducted passed the flaccid section 26.

Once a particular location of a collet 14 is established with respect to the inner tubular member 12, this collet 14 will remain in that position as long as it is unattended. This means that the volume of flow that is being conducted through the flaccid section 26 will also remain at its particular established level. It is to be understood that there inherently will be an outward pressure applied against the fingers 28 and 30 by reason of the small amount of pressurized fluid that is being conducted through the flaccid section 26. However, this pressure does not cause any 'creeping' rotational movement of the collet 14 relative to inner tubular bore 12. Also, because the section 26 is flaccid there is no memory tending to encourage expansion of this section back to the shape of the remaining portion of the tube 22. Therefore, there is no pressure tending to further encourage any rotation of the collet 14 relative to the inner tubular member 12 when left unattended.

It is to be noted that the collet 14 is of a length to extend past flaccid section 26. The flaccid section 26 has no strength or body itself. Therefore, if the collet 14 terminated in the area of the flaccid section 26, there would be a tendency for the tube 22 to kink. However, because the outer end of the collet 14 connects with the normal configuration of the tube 22, the inherent weakness of the flaccid section 26 is bypassed and kinking does not occur.

What is claimed is:

1. A flow control valve for regulating flow of a fluid through a flexible walled tubing, said flexible walled tubing having a rigid body, said flow control valve comprising:

an inner tubular member having a first axial bore, said inner tubular member including deflectable means;

a section of said flexible walled tubing located within said first axial bore, said section having an inner bore, said section being flaccid not having said rigid body, said section assuming a limp at rest position, said section being made flaccid by modifying of said section by treatment causing said section to lose its memory, said deflectable means being located directly adjacent said section; and a collet having a second axial bore, both said section and said inner tubular member being located within said second axial bore, said collet connecting with said inner tubular member by engaging means, said engaging means permitting longitudinal movement of said collet relative to said inner tubular member, said collet including cam means, said cam means being in contact with said deflectable means, whereby longitudinal movement of said collet relative to said inner tubular member is capable of causing said deflectable means to press against said section decreasing the cross-sectional size of said inner bore thereby decreasing the amount of fluid that can pass through said inner bore within a period of time.

2. The flow control valve as defined in claim 1 wherein:
said deflectable means comprising a pair of opposing fingers.

3. The flow control valve as defined in claim 2 wherein:
the interior surface of one of said fingers having a concave surface adapted to come into contact with said section, the interior surface of the other of said fingers having a convex surface adapted to come into contact with said section.

4. The flow control valve as defined in claim 3 wherein:
said engaging means comprising a screw thread assembly.

5. A flow control valve for regulating flow of a fluid through a flexible walled tubing comprising:
an inner tubular member having a first axial bore, said inner tubular member including deflectable means;
a section of said flexible walled tubing located within first axial bore, said section having an inner bore, said section being flaccid, said deflectable means being located directly adjacent said section;
said deflectable means comprising a pair of opposing fingers;
the interior surface of one of said fingers having a concave surface adapted to come into contact with said section, the interior surface of the other of said fingers having a convex surface adapted to come into contact with said section;
said engaging means comprising a screw thread assembly; and
said cam means comprising a conically tapered surface.

6. The flow control valve as defined in claim 1 wherein:
said treatment of said section is due to being thermally deformed to assume said flaccid configuration.

7. The flow control valve as defined in claim 1 wherein:
said inner tubular member being fixedly secured to said flexible walled tubing.

8. The flow control valve as defined in claim 1 wherein:
said collet having an outer free end, said outer free end being longitudinally spaced from said section to eliminate kinking of said flexible walled tubing with respect to said flow control valve.

9. A flow control valve for regulating flow of a fluid through a flexible walled tubing, said flexible walled tubing having a rigid body, said flow control valve comprising:
an inner tubular member having a first axial bore, said inner tubular member including deflectable means;
a section of said flexible walled tubing located within first axial bore, said section having an inner bore, said section being flaccid not having said rigid body, said section assuming a limp at-rest position, said section being made flaccid by modifying of said section by treatment causing said section to lose its memory, said deflectable means being located directly adjacent said section; and
force applying means located about said inner tubular member at said section, said force applying means for applying a force to said deflectable means which results in squeezing of said section thereby decreasing the cross-sectional size of said inner bore and decreasing the amount of fluid that can pass through said inner bore within a period of time.

10. The flow control valve as defined in claim 9 including:
means for fixing said force applying means to maintain constant the established level of flow of fluid through said inner bore.

11. The flow control valve as defined in claim 10 wherein:
said force applying means comprising a cam arrangement, said means for fixing comprising a threaded engagement between said inner tubular member and said force applying means, said threaded engagement permitting longitudinal movement of said force applying means relative to said inner tubular member.

* * * * *